United States Patent
Abolsky (10) Patent No.: US 11,980,831 B2
(45) Date of Patent: May 14, 2024

(54) METHOD AND APPARATUS FOR PURIFICATION AND REMINERALIZATION OF WATER

(71) Applicant: GENIVER LLC, Miami, FL (US)

(72) Inventor: Sebastián Abolsky, Ciudad Autónoma de Buenos Aires (AR)

(73) Assignee: GENIVER LLC, Miami, FL (US)

( * ) Notice: Subject to any disclaimer, the term of this patent is extended or adjusted under 35 U.S.C. 154(b) by 831 days.

(21) Appl. No.: 16/979,787

(22) PCT Filed: Mar. 12, 2019

(86) PCT No.: PCT/IB2019/052001
§ 371 (c)(1),
(2) Date: Sep. 10, 2020

(87) PCT Pub. No.: WO2019/175770
PCT Pub. Date: Sep. 19, 2019

(65) Prior Publication Data
US 2021/0016199 A1 Jan. 21, 2021

Related U.S. Application Data

(60) Provisional application No. 62/642,203, filed on Mar. 13, 2018.

(51) Int. Cl.
*B01D 1/06* (2006.01)
*A61L 2/10* (2006.01)
(Continued)

(52) U.S. Cl.
CPC ............... *B01D 1/065* (2013.01); *A61L 2/10* (2013.01); *A61L 2/18* (2013.01); *A61L 2/202* (2013.01); *A61L 2/26* (2013.01); *B01D 1/0017* (2013.01); *B01D 1/22* (2013.01); *B01D 5/006* (2013.01); *C02F 1/08* (2013.01); *C02F 1/32* (2013.01);
(Continued)

(58) Field of Classification Search
CPC .......... B01D 1/065; B01D 1/22; B01D 5/006; C02F 1/04; C02F 1/048; C02F 1/08; C02F 1/685; C02F 1/687
See application file for complete search history.

(56) References Cited

U.S. PATENT DOCUMENTS

| | | |
|---|---|---|
| 3,212,999 A | 10/1965 | Sommers |
| 3,393,130 A | 7/1968 | Meckler |

(Continued)

FOREIGN PATENT DOCUMENTS

| | | |
|---|---|---|
| DE | 102009010672 A1 | 10/2010 |
| WO | WO-1999/067004 A1 | 12/1999 |

(Continued)

*Primary Examiner* — Renee Robinson
(74) *Attorney, Agent, or Firm* — Muncy, Geissler, Olds & Lowe, P.C.

(57) ABSTRACT

A method and apparatus for water purification and remineralization are disclosed. The apparatus comprises a plurality of thermally coupled thermoelectric modules, as well as means for enhancing mass and energy transfers. The method provides a highly energy-efficient water purification process. The apparatuses and methods of the present inventions can be used to obtain purified and/or remineralized water at rates suitable for household water consumption.

17 Claims, 5 Drawing Sheets

(51) Int. Cl.
*A61L 2/18* (2006.01)
*A61L 2/20* (2006.01)
*A61L 2/26* (2006.01)
*B01D 1/00* (2006.01)
*B01D 1/22* (2006.01)
*B01D 5/00* (2006.01)
*C02F 1/08* (2023.01)
*C02F 1/32* (2023.01)
*C02F 1/68* (2023.01)
*C02F 1/76* (2023.01)
*C02F 1/78* (2023.01)
*A61L 101/06* (2006.01)

(52) U.S. Cl.
CPC ............... *C02F 1/685* (2013.01); *C02F 1/76* (2013.01); *C02F 1/78* (2013.01); *A61L 2101/06* (2020.08); *A61L 2202/11* (2013.01); *C02F 2201/782* (2013.01); *C02F 2303/04* (2013.01)

(56) References Cited

U.S. PATENT DOCUMENTS

| | | | |
|---|---|---|---|
| 3,801,284 A | 4/1974 | Meckler | |
| 4,584,061 A | 4/1986 | Shelton | |
| 6,695,951 B1 * | 2/2004 | Bitterly | B01D 3/10 |
| | | | 202/202 |
| 6,893,540 B2 | 5/2005 | Stout et al. | |
| 2006/0272933 A1 | 12/2006 | Domen | |
| 2009/0242485 A1 * | 10/2009 | Cabados | C02F 9/20 |
| | | | 210/652 |
| 2013/0243922 A1 | 9/2013 | Lynn | |
| 2014/0305789 A1 | 10/2014 | Lowenstein | |
| 2015/0360972 A1 * | 12/2015 | Reuveni | F28F 9/013 |
| | | | 202/241 |
| 2017/0291118 A1 * | 10/2017 | Sadegh | B01D 1/04 |

FOREIGN PATENT DOCUMENTS

| WO | WO-2001/045816 A1 | 6/2001 |
|---|---|---|
| WO | WO-2018/141883 A1 | 8/2018 |

* cited by examiner

METHOD AND APPARATUS FOR PURIFICATION AND REMINERALIZATION OF WATER

TECHNICAL FIELD OF THE INVENTION

The present invention relates to the field of purification and remineralization of water. In particular, the present invention is related to a method and apparatus for purification and remineralization of water comprising thermoelectric cells.

BACKGROUND

The consumption of bottled water has increased at much higher rates than the World population, with some sources estimating and forecasting a compounded annual growth rate of 8.5% between the years 2005 and 2020. In 2016, 300,000 million liters of bottled water were sold at an average selling price of 0.7 US dollars per liter. In that same year, the sold volume of bottled water surpassed that of carbonated soft drinks for the first time in the US. Essentially all bottled water is contained in single-use PET bottles. Only a small fraction of these PET bottles is recycled, and even when recycled, said recycled PET is eventually discarded.

The widespread use of PET bottles is associated with plastic microparticles in the oceans. Bottled water is often chosen by consumers chiefly due to its safeness and desirable taste and odor. Although tap water distributed in most developed countries satisfies the requirement of biological safeness, it may contain objectionable contaminants such as various chemicals, as well as objectionable odors reminiscent of chlorine, chloramine compounds or derivatives thereof. In developing countries, available water from the tap, river or well may not even be biologically safe.

Methods and apparatuses for purification and/or remineralization of water have been described in the patent literature.

U.S. Pat. No. 3,393,130 describes an apparatus for distilling saline water by employing thermoelectric heat pumps. Said thermoelectric heat pumps are configured in a concentric manner, so the heat flow at its ends cannot be recycled. This apparatus is difficult to be manufactured in industrial scale.

DE 10 2009 010 672 describes an arrangement of pool evaporators coupled to condensers by means of thermoelectric elements. Said arrangement is vertical, meaning that condensers are placed above evaporators. This arrangement requires that the condensing fluid be captured by a tray, which may disrupt the upward flow of vapors and moreover introduce unfavorable separation between evaporation and condensation elements. Free convective heat flow inside pool evaporators tends to be slow, meaning that a large temperature gradient is required, resulting in low heat pump efficiencies. Moreover, said vertical arrangement makes it impossible to efficiently close the thermal circuit, i.e. exchanging heat between the end hot surface and the end cold surface.

U.S. Pat. No. 6,893,540 describes a distillation unit that comprises a thermoelectric cooler. This invention requires that the water be boiled and then condensed. However, it is known that thermoelectric coolers are severely inefficient when the temperature difference between both of its ends is above approximately 30° C. The objects described in this document can be considered energy inefficient.

U.S. Pat. No. 4,584,061 describes a vacuum desalinization device, wherein salty water is boiled and condensed under a vacuum, with a condenser above the evaporation chamber. The objects disclosed in the documents share many of the disadvantages discussed earlier for document DE 10 2009 010 672.

WO 2018/141883 describes an apparatus for distilling water comprising discrete, vertically arranged pool evaporation and condensation sections, where only latent heat is partially recovered. By virtue of said vertical arrangement, the produced vapor is required to flow downwards, which is physically unfavorable. Moreover, the described apparatus effects the evaporation at nearly 100° C., inducing the formation of carbonaceous scale. The apparatus includes a refrigeration cycle, and must be cast or machined from solid metal blocks, rendering it impractical for high-scale commercial applications.

U.S. Pat. No. 3,212,999 describes an apparatus comprising discrete pool boiling and condensation chambers, separated by thermoelectrically active elements. Water vapor must flow upwards and then downwards into the condensation chamber in order to produce the desired effect. As disclosed, the apparatus is essentially impossible to disassemble, and the flow of vapor is severely constrained.

WO 1999/067004 describes an apparatus and method for purifying and cooling a liquid comprising two discrete evaporation and condensation chambers contacting a same thermoelectrically active element. Although it is claimed that the apparatus is modular, it is to be understood that its modularity can be achieved by placing several of these apparatuses together.

WO 2001/045816 describes an apparatus for distilling water by pool boiling inlet water at a temperature of between 97 and 100° C., coupling boiling and condensation on the same thermoelectrically active element. The water vapor is expected to flow inside an intricate construction involving several sharp turns, going upwards and downwards, which is considered unfavorable for all practical applications.

US 2014/0305789 describes an apparatus for separating components from a liquid mixture by means of diffusion gap vaporization/condensation. Although the described apparatus presents an arrangement in series, no active element is used to recover the latent heat involved, nor is the apparatus modular or enabled for its easy disassembly and maintenance.

There is therefore a need to provide methods and apparatuses for purification and/or remineralization of water that address the disadvantages of the prior art, in particular those related to process efficiency and ease of maintenance.

SUMMARY OF THE INVENTION

The objectives of the present invention are to provide simple, energy-efficient, easily maintainable, and inexpensive methods and apparatuses for obtaining high-quality water directly at or near the point of use, starting from a feed of raw water to be purified.

Said objectives are achieved by incorporating elements for enhanced mass and energy transfer phenomena within a series of thermally coupled thermoelectric cells, as disclosed herein. Surprisingly, the incorporation of said elements allow for an overall highly energy-efficient purification and/or remineralization of raw water at unusually low temperatures, i.e. lower than the boiling point of water at the prevailing pressure, resulting in various advantageous characteristics. Moreover, the disclosed physical construction results in an easy sanitation of the inner parts, which was not approached, disclosed nor resolved in the prior art. The unusual and not previously discussed, advantageous characteristics include, but are not limited to (a) the modular nature of the apparatus, which favors its industrial construction, packing, shipping, and scale-up, (b) the disassemblable nature of the apparatus, which enables that the inner parts be washed by hand by an end user or in a dish-washing machine, (c) the easy addition of new or removal of faulty modules in order to increase, decrease, or repair a working apparatus, (d) the added roughness of the surfaces comprising falling film or wet evaporation elements, so that the minimum wetting rate is lowered to practically useful flow rates.

By using the methods and apparatuses of the present invention, the need for sourcing, transportation, stocking, distribution, usage of plastic bottles, and selling of drinking water can be substantially minimized or eliminated.

It is therefore an object of the present invention to provide an apparatus for purification and/or remineralization of water comprising a plurality of thermoelectric modules in a horizontal arrangement, each of said modules comprising a hot side and a cold side, wherein at least a first hot surface is thermally coupled to said hot side and at least a first cold surface is thermally coupled to said cold side, said hot surface comprising means for contacting a liquid to said first hot surface, said means being selected from a falling film element or a porous, fibrous, fritted, sintered, patterned, finned, or carved wet evaporation element.

In a preferred embodiment of the apparatus of the present invention, the separation between said hot surface and said cold surface is between 1 and 40 mm.

In another preferred embodiment of the apparatus of the present invention, the separation between said hot surface and said cold surface is between 5 and 15 mm.

In yet another preferred embodiment of the apparatus of the present invention, the temperature of said hot surface, depending on the position of the thermoelectric module within the train, is in the range of approximately 30 to 100° C., preferably between 40 to 70° C., and in a similar way, the temperature of said cold surface, depending on the position of the thermoelectric module within the train, is in the range of approximately 10 to 90° C., preferably 20 to 50° C.

In yet another preferred embodiment of the apparatus of the present invention, said apparatus further comprises a disinfecting element selected from the group consisting of a UV-lamp, a hypochlorite generator, a mixed oxidants generator, and an ozone generator.

In another preferred embodiment of the apparatus of the present invention, at least one of the hot surface or the cold surface is made from a metallic material or a thermoplastic polymer material.

In yet another preferred embodiment of the apparatus of the present invention, said metallic material is selected from the group consisting of stainless steel of various grades, titanium, copper, aluminum, brass and bronze. The corresponding surface may be roughened so that the minimum wetting rate of the falling film is reduced.

In a preferred embodiment of the apparatus of the present invention, each of said thermoelectric modules comprises one evaporation half-cell and one condensation half-cell on opposing sides, and a distillation cell is configured by the assembly of two half-cells comprised in two contiguous thermoelectric modules, each of said thermoelectric modules comprising sealing means so that moisture, water jets or sprays may not enter. The sealing means may comprise adhesives or mechanical seals.

In yet another preferred embodiment of the apparatus of the present invention, said material is polypropylene or polyethylene or mixtures thereof.

In another preferred embodiment of the apparatus of the present invention, said material further comprises copper-, graphite-, or nickel-based particles.

It is another object of the present invention to provide a method for purification of water, comprising the steps of:
  feeding a raw water feed to an apparatus for purification and/or remineralization of water according to the present invention,
  contacting at least a portion of said inlet raw water feed to at least a hot surface,
  evaporating at least a part of said portion of said inlet raw water feed to obtain a vapor stream,
  transporting said vapor stream to at least a cold surface, and
  condensing said vapor stream at said cold surface In another preferred embodiment of the method of the present invention, the evaporating step is carried out at a temperature in the range of approximately 30 to 100° C.

In yet another preferred embodiment of the method of the present invention, the condensing step is carried out at a temperature in the range of approximately 10 to 90° C.

In another preferred embodiment of the method of the present invention, the condensing step is carried out at a temperature in the range of approximately 20 to 50° C.

In yet another preferred embodiment of the method of the present invention, the method further comprises the step of remineralizing said condensed vapor stream.

In another preferred embodiment of the method of the present invention the remineralization step is carried out in a vessel external to said apparatus.

DETAILED DESCRIPTION

The present invention will be described in detail below, with reference to the figures and examples, which are included only for the purpose of illustrating the invention and are not to be construed as limiting thereof.

The term "approximately" as used herein when referring to a measurable value means that it comprises variations of ±10% from the specified amount.

As used herein, the terms "comprises", "has" and "includes" and their conjugations mean "including but not limited to".

As used herein, the term "purification" refers to the removal of impurities, minerals and/or electrolytes from a raw water feed. The products obtained with such processes are commonly known as "purified water", "demineralized water", "distilled water", which are used interchangeably herein.

The term "raw water" as used herein refers in general to non-drinkable, containing impurities or at least objectionable water-containing liquids, such as for example seawater, brackish water, underground water, tap water, urine or rainwater. The term "impurities" refers to various organic or inorganic salts, dissolved gases, particulate matter, or substances more or less volatile than water such as for example 1,2-dichloroethane, N-nitrosodimethylamine or derivatives thereof.

As used herein, the term "remineralization" refers to the addition of compounds to previously purified water. The term should be interpreted in a broad manner, not necessarily strictly limited to minerals, but rather to the addition of any compound which may be considered reasonable or desirable in the water. For example, carbonation salts, flavoring agents, sugar, coloring agents may as well be added.

The term "thermoelectric module" as used herein refers to a device comprising thermoelectric elements, such as a Peltier cell, which can act as a heat pump, in general transferring heat from a cold reservoir or "cold side" or to a hot reservoir or "hot side", and through the condensation and evaporation of a liquid, in particular water, in air on respective half-cells on opposing sides.

As used herein, the term "cell" refers to a repeating unit comprising at least a first hot surface thermally coupled to a hot side of a first thermoelectric module and at least a first cold surface thermally coupled to a cold side of a second thermoelectric module.

As used herein, the term "thermally coupled" refers to a relationship of identified components of the present invention such that thermal energy can be transferred from one element to another component, e.g. by thermal conduction.

As used herein, the term "horizontally arranged" or "horizontal arrangement" means that all the thermoelectric modules or cells in the apparatus are disposed substantially in the same horizontal plane, with their hot and cold sides perpendicular to said plane.

The term "means for contacting a liquid" as used herein refers to elements used to drive a liquid in contact with a given surface, in particular with a hot surface over which an evaporation phenomenon may take place. For example, said contact may be in the form of a free-falling film of liquid in contact with a surface when using a "liquid film evaporation element", such as a nozzle or conduit positioned such that the liquid falls over the surface forming a free-falling film, or said contact may be driven by capillary effect using a "wet evaporation element", as will be described herein. The term "condensation elements" as used herein refers to elements used to recover a condensed vapor stream, such as a tray.

As used herein, the term "evaporation" means the transition of at least some amount of a substance from a liquid phase into a gas phase, without the vapor pressure of said substance necessarily being greater or equal than the prevailing pressure. Similarly, the term "condensation" means the transition of at least some amount of substance from a gas phase into a liquid phase, without the vapor pressure of said substance necessarily being lower or equal than the prevailing pressure. In this manner, the terms "evaporation" and "condensation" are respectively related to the terms "humidification" and "dehumidification", commonly used for systems comprising water and air.

The terms "water vapor" or "vapor stream" as used herein refer in general to water in the gaseous phase and possibly at least another gaseous substance or substances, either condensable or not, such as air. The terms should not be interpreted in the strict sense that they refer exclusively to water.

Figure 1:
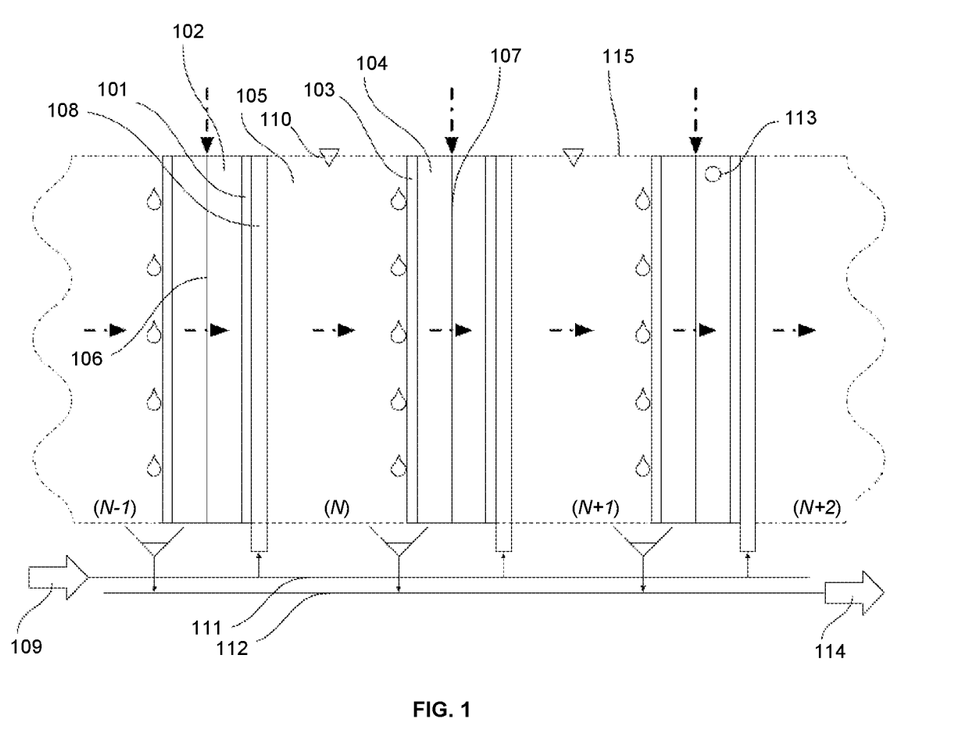
FIG. 1 is a side view of a preferred embodiment of the apparatus of the present invention comprising a wet evaporation element.

In the exemplary embodiment of the present invention shown in FIG. 1, the apparatus comprises a train of a number $N_{total}$ of cells ranging from 6 to 60 thermodynamically coupled cells, preferably 10 to 20 cells. In FIG. 1, cells N and N+1 are represented, along with a portion of cells N−1 and N+2, N being a numeral ranging from 2 to $N_{total}$−2. Each cell such as N comprises at least a hot surface 101 suitable for exchanging heat with the inside 105 of cell N, and at least a cold surface 103 suitable for exchanging heat with the same inside 105 of cell N, said at least first hot surface 101 being thermally coupled to at least the hot side 102 of at least one adjacent thermoelectric element 106, and said at least a first cold surface 103 being thermally coupled to at least the cold side 104 of at least one other adjacent thermoelectric element 107.

Figure 2:
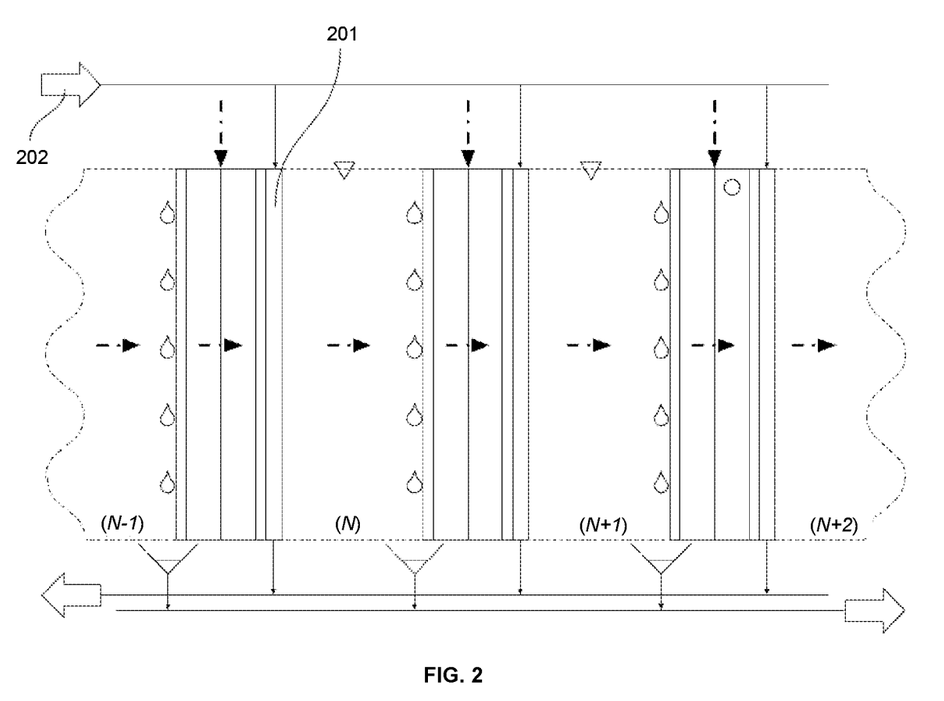
FIG. 2 is a side view of a preferred embodiment of the apparatus of the present invention comprising a falling film evaporation element.

In such an embodiment, the train may not be thermally closed, meaning that hot surface 101 of cell 1 may be thermally insulated from the exterior, and either be heated by means of a heating element other than a thermoelectric element, or not be heated and instead solely function as a mechanical element for supporting evaporation element 108 or evaporation element 201 in FIG. 2, while the water recirculating inside the apparatus is at a high enough temperature to effect at least some of the desired evaporation inside said cell 1. Similarly, cold surface 103 of cell $N_{total}$ may be cooled by means of a cooling fan, passive cooling fins, or by contacting the outer surface with cold inlet raw water to effect at least some of the desired condensation inside said cell $N_{total}$.

The evaporation of water at said hot surface 101 generates a vapor stream that is transported through the inside 105 of the cell towards said first cold surface 103. Said water vapor is condensed at said first cold surface 103.

In such an arrangement, the heat released, i.e. latent heat by condensation, in cell N−1 is absorbed by cell N, and the heat released in cell N is absorbed by cell N+1. This is illustrated by the horizontal arrows representing the convective and condensation heat transfer between adjacent cells, as well as the conductive heat transfer inside the thermoelectric modules. The vertical arrows represent electrical work consumed by the thermoelectric elements.

Said cold 103 and hot surfaces 101 may be substantially flat and are not necessarily parallel to each other nor in general necessarily parallel to any other of the cold or hot surfaces in the train. The separation between cold 103 and hot 101 surfaces of any one cell is between 1 and 40 mm, preferably 5 to 15 mm. Said separation forms a thin chamber filled with an inert gas substantially insoluble in feed water, preferably air, possibly further including gases evacuated from the raw water.

Water vapor is generated at the hot surfaces by various mechanisms, chiefly by the skin evaporation of water, due to the vapor pressure of water being above the partial pressure of water inside the chamber, but possibly in addition due to pool boiling or nucleation of vapor bubbles on the surface of rough elements.

The generated water vapor is transported downgradient through said chamber filled with an inert gas, from a moisture-rich zone near a hot surface to a moisture-depleted zone near a cold surface. Since the transport of said water vapor takes place downgradient naturally, i.e. it may not be assisted or forced through, it is advantageous that said chamber be as thin as possible, so that the transport is enhanced. The rate of transport is, to a good approximation, inversely proportional to said thickness.

The horizontal train configuration disclosed herein allows such advantageous construction of thin chambers. Hot 101 and cold 103 surfaces should intimately contact hot 102 and cold 104 sides, respectively, of a cell. Said intimate contact may be achieved by (a) direct contact, (b) pressing with the aid of rivets, screws or elastic elements, (c) the outward, elastic deformation of a casing which presses the surfaces upon relaxation, (d) the addition of a thermally conductive grease, adhesive, silicone, or graphite, (e) any combination of methods (a) through (d).

It is advantageous that evaporation and condensation surfaces be facing each other and as close as possible, in order to enhance the rate of condensation. Some arrangements of the prior art are disadvantageous, in that they require that moist air travel upwards and then downwards in order to condense on a surface far removed from the evaporation surface. In the absence of an imposed pressure gradient, this results in a very low condensation rate for practical purposes.

The width and height of hot and cold surfaces should roughly match the dimensions of the hot and cold sides of the employed thermoelectric elements. When commercially available thermoelectric elements are used, width typically ranges between 20 and 200 mm. It follows that the width of hot and cold surfaces ranges between 20 and 250 mm, preferably between 20 and 80 mm. Heights present similar values.

It is advantageous that the thickness of hot and cold surfaces be as thin as feasible, so that the thermal gradient is as flat as possible for any given thermal flux in units of power per unit surface area. When the surface has a low thermal conductivity, e.g. 1 W/mK or lower, thickness is between 0.1 and 2 mm, preferably 0.1 to 0.5 mm. When the surface has a high thermal conductivity, e.g. 50 W/mK, thickness is between 0.1 and 5 mm, preferably 1 to 3 mm.

The cells further comprise porous, fibrous, fritted, sintered, patterned, finned, or carved wet evaporation elements 108, coupled to at least a first hot surface 101 so that inlet raw water feed 109 may at least partially rise by capillary effect and wet at least partially said element, thereby enhancing the contact area between hot surface 101 and feed 109. Said evaporation elements 108 may be made of (a) inert polymers such as polytetrafluoroethylene, polyethylene, polypropylene (b) metallic or ceramic sponges, porous, or sintered porous materials, (c) embossed polymers or metals, (d) patterned surfaces obtained in injection molding, (e) fibers bonded together thermally, mechanically or chemically. Said cell may further comprise venting valves 110, a feed distributor 111, means 112 of collecting condensate 114, various thermometers 113 as well as other sensing elements or arrangements, including humidity sensors, manometers, heat flux meters and the like. The train may further comprise insulating material or materials 115 at least partially surrounding the exterior walls, so that a satisfactory thermal efficiency is obtained. Additionally, some parts may be left exposed to the atmosphere or in contact with heat sinks, either active or passive, so that a correct heat balance inside each cell may be obtained. In effect, each heat pump is introducing more heat than it absorbs, at a ratio of (COP+1)/COP. An advantageous characteristic of the present arrangement is the possibility for this additional heat to be easily controlled.

Since the inlet feed 109 may contain pathogens or dissolved or non-dissolved non-volatile substances such as various salts, particulate matter or scale-forming carbonates or alkaline cations, it may be advantageous to wash the cell and, in particular, the porous, fibrous, fritted, sintered, patterned, finned, or carved wet evaporation element 108, so that said non-volatile substances do not accumulate during sustained operation or that having accumulated they may be satisfactorily removed or at least diagnosed. In order for said wash to be effective, the inlet feed 109 may be introduced in a controlled manner, thereby flooding said cells and effecting said wash. Said wash may be effected periodically or when deemed necessary, for example following usage estimates, or using heat flux or conductivity sensors. In one exemplary application, thermoelectric module 106 is suddenly operated in reverse, i.e. allowed to generate work (e.g. electric work) from the transport of thermal energy. A characteristic decay curve of, for example, voltage and/or current as a function of time may be obtained. Said characteristic decay curve may be correlated to various fouling situations, typically the transport of thermal energy being slower with increasing fouling of the cell. In another exemplary application, the buildup of substances in wet evaporation element 108 is measured by measuring the electrical conductivity of the liquids wetting said element 108. Typically, conductivity is positively correlated to fouling or at least the buildup of conductive substances, such as salts.

When operating under approximately atmospheric pressure conditions, evaporation may be effected at a temperature in a range of approximately 30 to 100° C., preferably between 40 and 70° C., so that the generation of carbonaceous deposits is minimized while maintaining a reasonably high evaporation rate and displacing at least some of the air inside the cell, which would otherwise reduce the overall efficiency by exchanging sensible heat between the hot and cold surfaces.

Condensation may be effected at a temperature in a range of approximately 10 to 90° C., preferably between 20 and 50° C., the condensing temperature on a cold surface of a cell being lower than the evaporating temperature of a hot surface of said cell.

The temperature difference between any two hot and cold sides of any given cell is of about 1 to 40° C., preferably 10 to 20° C., so that said heat pump works with a reasonably good thermal efficiency or high coefficient of performance (COP) of at least above 1, and preferably between 2 and 7. Commercially available thermoelectric devices, such as Thermonamic TEC1 series, can achieve COP values in the range of 2-5 when the temperature difference between the hot and cold sides is in the range of 5-20° C. and the heat absorbed on the cold side is about 5-50 W.

For any given finite heat flux (power per unit surface area), there will exist some temperature gradient inside evaporation and condensation elements. Thus, the temperature difference between evaporation and condensation will, in general, be smaller than the temperature difference between the hot and cold sides of the heat pumps. Said temperature difference between evaporation and condensation is of about 0.1 to 20° C., preferably 0.5 to 10° C.

Other values may be obtained using different thermoelectric devices. Moreover, advances in technology or manufacturing will surely make more efficient and powerful thermoelectric modules readily available.

In another embodiment, no additional hot surface 101 or cold surface 103 is coupled to the heat pump 106 or 107. Instead, any said heat pump is directly exposed to vapor and condensate in 105. In this case, the apparatus may be manufactured more easily.

In another exemplary embodiment shown in FIG. 2, the apparatus comprises a falling film evaporation element 201 such that the inlet feed 202 is introduced from the top by means of a liquid distributor and allowed to form a free-falling film of water on each hot surface at which at least a fraction of said film is evaporated. A recirculation pump can be used to recycle the non-evaporated fraction to the inlet feed.

In another embodiment, a disinfecting agent is added in at least one point of the system to disinfect some of its elements. Said disinfecting agent, such as hypochlorite, may be generated in situ, for example through the electrolysis of chloride-rich water or through the electrolysis of the feed raw water, which may contain useful or additioned quantities of chloride.

In another embodiment, a disinfecting element, such as a UV-lamp, a hypochlorite generator, a mixed oxidants generator, or an ozone generator, is included in at least one of the cells so that it may be used to disinfect some of the elements.

In another embodiment, at least a first hot surface or at least a first cold surface is made from a metallic material or a thermoplastic polymer material, such as stainless steel of various grades, titanium, copper, aluminum, brass or bronze, or polypropylene, polyethylene, optionally including heat-conducting enhancers, such as copper-, graphite-, or nickel-based particles. With the use of said polymer material, corrosion is minimized with respect to bare metallic elements, comprising for example aluminum or copper.

In another embodiment, said first hot surface may have an average surface roughness ($R_a$) of between 1.2 and 50 micrometers, so that the minimum wetting rate of the falling film is reduced, enabling a lower steady-state flow rate of water inside the apparatus. The minimum wetting rate is the flow rate (in units of mass per unit time and per unit length perpendicular to the flow) which produces a falling film which covers substantially most or all of the available surface over which it is falling. Surprisingly, the minimum wetting rate of a falling film shows a strong hysteresis in the domain of surface area covered as a function of flow rate, meaning that a higher flow rate may be initially required to cover most or all of the surface of the metallic material with a falling film, but it may then be safely lowered down to a lower certain value without substantially destroying the formed film. Due to said hysteresis phenomenon, said lower certain value may be from 1.5 to even 5 times lower than the flow rate required to initially form the falling film.

In another embodiment, said average surface roughness may be further bounded to between 2 and 20 micrometers and said lower certain value to between 2 and 3 times lower than the initial minimum wetting rate.

In another embodiment, at least some parts of the apparatus are one-piece molded by injection, said piece containing slits where the thermoelectric modules may be introduced.

In another embodiment, at least some parts of the apparatus are detachable and dishwasher-safe. It is unique to the construction of the apparatus of the present invention that the distillation cells are not discretely constructed or manufactured, instead they materialize only when two contiguous half-cells, one evaporation half-cell and one condensation half-cell, are assembled, while being completely exposed when disassembled. Advantageously, an end user can thus disassemble, wash, clean, sanitize, inspect, store and replace elements if so desired. As previously indicated, a distinctive characteristic of the disclosed apparatus is that it comprises a train of $N_{total}$ distillation cells which materialize only when two contiguous half-cells, one evaporation half-cell and one condensation half-cell, which are physically part of the same module and whose active surfaces are respectively on opposing sides of the module, are assembled in a manner described herein, exposing said surfaces when disassembled, and protecting the thermoelectric element inside. The assembly and disassembly of any two half-cells comprised in two contiguous individual thermoelectric modules can be easily carried out.

In another embodiment, the train is connected to at least a compressor, vacuum pump, ejector, cold-condensing surface, cylinder and piston, or similar means. This allows the inner pressure to be set at pre-determined values, in particular different than atmospheric.

In another embodiment, the train further comprises thermometers attached to at least some of the hot or cold surfaces. Said thermometers relay their temperature readings to a processing unit which controls the steady operation of the train chiefly by controlling the power supplied to each thermoelectric element. In a simple control loop, if the temperature of a hot surface is decreasing, the power supplied to its corresponding thermoelectric element may be increased. It should be taken into account that, when its supplied power is increased, the temperature on its cold surface may simultaneously decrease. Alternatively, if the temperature of a cold surface is increasing, the power supplied to its corresponding thermoelectric element may be increased. Thus, the processing unit must model the complete train in order to successfully control the operation of the train. Said processing unit may further control liquid levels by controlling pumps or valves, thickness of falling films by controlling pumps or valves, or pressures by controlling vents.

Figure 3:
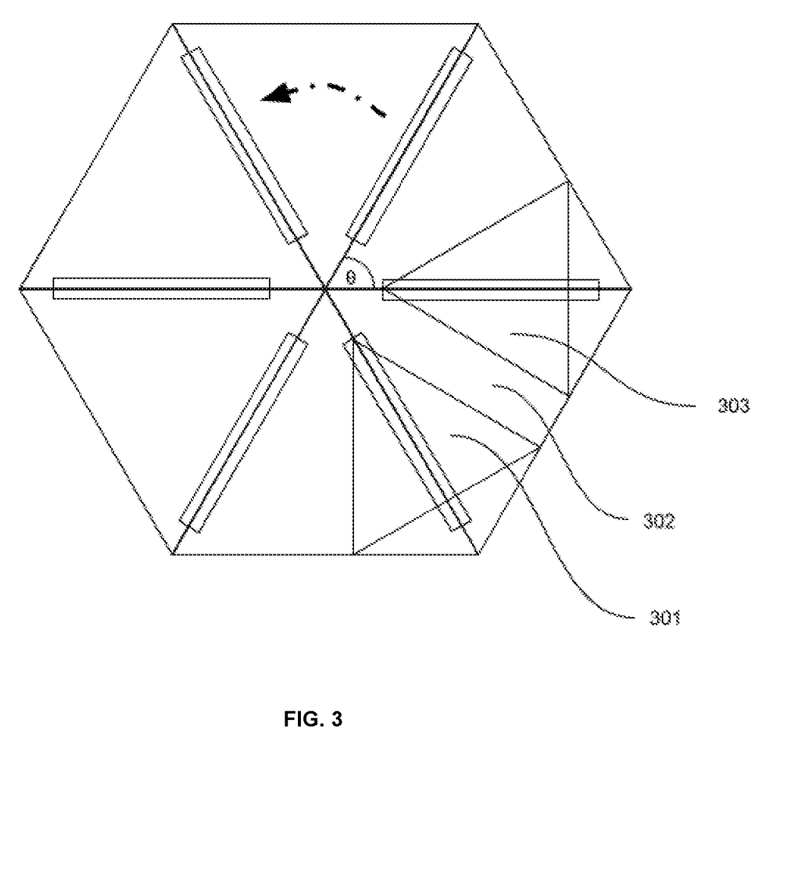
FIG. 3 is a top view of a preferred embodiment of a regular 6-cell apparatus of the present invention.
Figure 4:
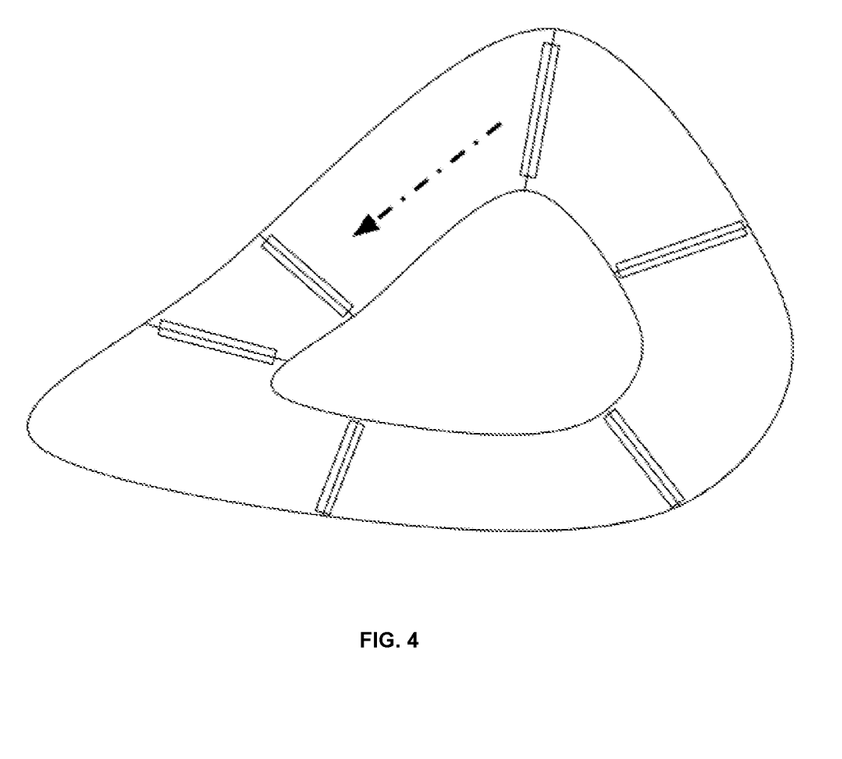
FIG. 4 is a top view of a general embodiment of an irregular, thermally closed apparatus of the present invention.

In another exemplary embodiment shown in FIG. 3, the train of thermally coupled cells is arranged such that the train is thermally closed describing a continuous path, i.e. any given cell is able to exchange heat with at least two other cells, meaning there are no cold- or hot-ends, which may happen for example if the train were a straight line of cells. One example of such an arrangement not containing cold- or hot-ends may be one in the form of a ring or cake, wherein each roughly-triangular slice contains at least one cell. For purposes of simplicity, the exemplary embodiment in FIG. 3 shows 6 cells. Less or more than 6 cells may be contained in other such arrangements. Each said roughly-triangular slice should be such that the chamber formed between hot and cold surfaces is thin, as previously discussed. In order for the mass transfer through chamber 302 to be homogeneous, the surfaces where evaporation and condensation take place may be parallel to each other. Both characteristics may be achieved by employing a small angle θ. Alternatively or simultaneously, the wet evaporation elements 301 and condensation elements 303 may be in the shape of a counter-triangle so as to counter-act the angled shape given by triangular slices. Thus, the thin chamber or space 302 between hot and cold surfaces is parallel even though hot and cold sides are not. When commercially available thermoelectric elements are employed, depending on the distance to the center of the pie, the angle θ of a triangular slice may reach approximately between 1° and 30°, preferably between 6° and 15°. A complete pie covers the full circular arc, i.e. 360°. Thus, the number of cells in a complete pie is 360/θ. 1° translates to 360, 30° to 12, 6° to 60, and 15° to 24. Said closed arrangement need not necessarily be regular, as shown in FIG. 4.

Figure 5:
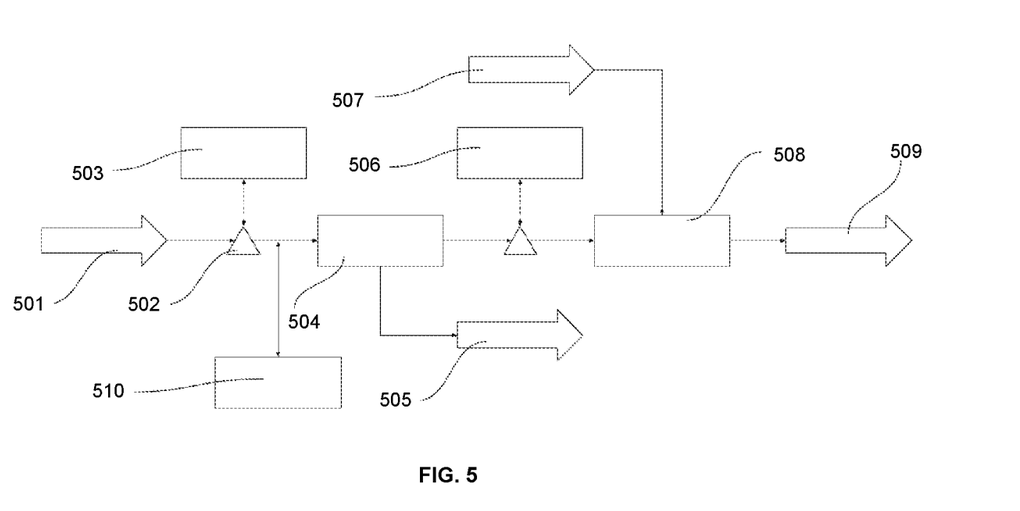
FIG. 5 is a flow diagram representative of the purification/remineralization method of the present invention.

In the exemplary embodiment shown in FIG. 5, the method comprises the step of receiving possibly non-drinkable, impure or at least objectionable water-containing liquids 501, such as for example seawater, brackish water, underground water, tap water, urine, rainwater, sewage, greywaters. Said water-containing liquids may be stored in a tank 503 for its immediate or further use. Either directly through valve 502 or from said tank 503, said water-containing liquids are then fed to a purification unit 504 which substantially strips said liquids of essentially all their compounds other than molecular water (i.e. $H_2O$) itself, including but not limited to for example ions such as commonly-occurring lithium ($Li^+$), sodium ($Na^+$), potassium ($K^+$), magnesium ($Mg^{2+}$), calcium ($Ca^{2+}$), fluoride (F), chloride ($Cl^-$), sulfate ($SO_4^{2-}$), sulfite ($SO_3^-$), nitrate ($NO_3^-$), nitrite ($NO2^-$), carbonate ($CO_3^{2-}$), bicarbonate ($HCO3^-$), phosphates ($H_xPO_4^{(3-x)-}$), hypochlorite ($ClO^-$), chlorate ($ClO_3^-$); primary-, secondary-, tertiary-chloramines or chloroamine ($H_2NCl$); metal and metalloid compounds of chromium (Cr), manganese (Mn), iron (Fe), cobalt (Co), copper (Cu), zinc (Zn), aluminum (Al), arsenic (As), mercury (Hg), lead (Pb) either as the pure ions, hydroxides, hydrates, complexed ions or derivatives thereof. Said compounds other than molecular water may further comprise compounds such as alcohols, acids, bases, phenols, oils, hydrocarbons, aromatics, waxes, dissolved gases, particulate matter, suspended solids, urea, viruses, bacteria, cysts, pathogens, miscible or partially-miscible liquids such as perfluorooctanoic acid (PFOA), N-nitrosodimethylamine (NDMA), N-nitrosodiethylamine (NDEA), or other nitrosamines.

Said compounds, either with at least enough water to maintain them in a dissolved or suspended state, or in their gaseous form, are removed or purged through purge 505 from the system following a continuous, batch or semi-batch step.

If said step consists of a continuous process, a fraction of the liquids fed to the purification apparatus is discarded as purge 505 after being enriched in said compounds. For example, there may be 1 part contaminant for each 100 parts raw feed water. Following one or more purification step, there may remain, for example, 1 part contaminant for each 20 parts raw water in some given vessel or position within the apparatus, i.e. the apparatus successfully enriches raw water in contaminants by removing substantially pure water, which is subsequently obtained as a desired substance. The water enriched in contaminants thus obtained, which may contain different concentrations of contaminants, is purged from the system into, for example, a drainage, so as to maintain a time-averaged steady-state mass balance inside the apparatus.

If said step consists of a batch or semi-batch process, said compounds may be removed during a washing step, wherein some elements in the purification unit which had been progressively enriched in said compounds, for example a filter, an ion-exchange membrane or resin, a vessel from which water is evaporated, a porous wet evaporation element from which water is evaporated, are washed with enough feed liquids so as to dissolve, dilute, or drag said compounds. Alternatively, said enriched liquid may simply be discharged without further dilution or washing.

In another embodiment, the raw water is subjected to a stripping step 510, wherein at least some volatile compounds which may be present are at least partially removed, such as ammonia, oxygen, carbon dioxide, benzene, carbon tetrachloride, 1,2-dichloroethane, ethylbenzene, toluene, or possibly less volatile contaminants such as atrazine, carbofuran, diquat or lindane.

Said stripping step may be carried out by venting at least part of the gas phase in contact with the inlet raw water feed before (as in FIG. 5) it is subjected to further purification, between purification steps, or after water is purified of its non-volatile contaminants. Said stripping step may further comprise heating, either using an electric heating element, the hot side of a thermoelectric element or by recovering heat from other parts of an apparatus, flashing at a lower pressure and pumping, pumping to a higher pressure and flashing, spraying or aerating in contact with a carrier gas such as air, either under natural or forced convection. Stripping rates may be estimated by means of the Henry's law approximation for infinite dilutions.

Said stripping step may aid in the equalization of temperatures by removing latent heat and thus maintaining the heat balance across the apparatus. An evaporation of about 1% of the inlet flow approximately coincides with the excess heat introduced by the heat pumps of thermodynamic efficiency in general lower than 1 and by definition equal to (COP+1)/COP.

In another embodiment, purified water is obtained by evaporating the inlet raw water feed by heating with an electric heating element, wherein said evaporation may take place at or below the boiling point of the liquids at the prevailing pressure. Produced vapors are condensed by rejecting heat to the surrounding atmosphere. Purification of water may further comprise a stripping step of at least some volatile compounds.

If it is required to remove solid compounds which may have irreversibly precipitated from solution such as for example $CaCO_3$, $MgCO_3$, chemicals such as acids, bases or other cleaning agents may be added.

Furthermore, if pathogen removal is required, chemicals such as hypochlorite, hypobromite, hydrogen peroxide may be added.

Alternatively, parts of the system may be subjected to high temperature or radiation such as UV or gamma-rays to obtain a disinfection effect.

Obtained purified water may be stored in a tank 506 or used immediately. The present invention provides water of favorable quality ready for consumption.

Said purified water is devoid of any minerals which give water its desirable, agreeable odor and flavor, as well as sufficient electrolytes required in a balanced diet.

Said purified water may be remineralized in remineralization step 508 so that its electrolyte composition or organoleptic characteristics are enhanced, possibly reaching or even surpassing objective and subjective properties found in the best available mineral waters. High-quality remineralized water 509 is obtained as the final product of the method.

Remineralization may be effected by dissolving a pill of a pre-formulated composition in a vessel external to the apparatus, or it may be effected by the manual or automatic dosing 507 of a pre-formulated powder or its solution in concentrated form, either in-line or in a vessel, either inside or outside the apparatus, or it may be effected by guiding or forcing said purified water through a capsule, pod, permeable bag, ion-exchange resin, or similar element containing a pre-formulated composition of minerals and chemicals, in a manner resembling that of capsule-based coffee machines.

An assortment of various formulations may be available, so that for example waters sourced from Fiji or Évian-les-Bains may be exactly replicated by adding the precise quantities of each of the compounds and gases.

EXAMPLES

Energy Performance

The energy performance of a method and apparatus of the present invention was compared to that of water purification and/or remineralization devices from the prior art.

The apparatus of the present invention was manufactured using TEC1-12706 thermoelectric elements. The experimental conditions corresponded to COP values of approximately 3, 4 and 5.

Each cell of the apparatus comprised a wet evaporation element made from machined aluminum and a porous synthetic sheet of approximately 2 mm thickness in intimate contact, and a condensation element made from similarly machined aluminum. Both elements were in intimate contact with each thermoelectric element. The complete train comprised 3 such cells pressed together by means of an external clamp. Raw water was fed by means of a hose connected to feed holes passing through each aluminum element and correspondingly contacting each porous synthetic sheet, which took up water by capillary and wetting effects, while maintaining an external liquid level so that the wet evaporation elements were always kept wet. Condensate was similarly collected by means of another hose connected to holes passing through each aluminum element and correspondingly collecting condensate dripping from each condensation element. Temperatures were measured internally with calibrated thermocouples and also externally with IR sensors. Being a thermally open loop, heat was supplied to the cold side of a terminal thermoelectric module with an electric resistance, and heat was similarly removed from the hot side of the other terminal thermoelectric module with a cooling fan.

Device 1 is an electrical heating element (i.e. heating coil) used to evaporate raw water, with condensation as a separate operation.

Device 2 is a DV-4 distiller as available from Kambič d.o.o.

Device 3 is a 4 L distiller as available from Life Basis. The obtained energy consumptions for purifying 1 kg of water at 25° C. and 1 atm are shown in Table 1.

TABLE 1

Comparison of the present invention and prior art for purification of water

|  | Device 1 | Device 2 | Device 3 | Invention (COP = 3) | Invention (COP = 4) | Invention (COP = 5) |
|---|---|---|---|---|---|---|
| Energy consumption (kWh) | 0.715 | 0.750 | 0.750 | 0.218 | 0.164 | 0.131 |

It was found that using the present invention in conditions such that 15 W of heat are absorbed at the cold surface, approximately 520 g of distilled water are obtained per day per cell, in a continuous operation.

The method of the present invention is therefore more energy-efficient than those of the prior art. The apparatuses and methods of the present inventions can be used to obtain purified and/or remineralized water at rates suitable for household water consumption, thereby reducing the need of PET materials for packaging and distribution.

Surface Roughness

Commercially available SAE 304 and SAE 316 stainless steel sheets were cut, roughened to approximately $R_a$=12.5 micrometers, as determined by comparing to standard samples, and placed in a falling film setup including a regulated recirculation pump, water reservoir, thermometer and water distributor. The initial minimum wetting was measured as about 0.12 kg/cm-min and, in this particular setup, substantial wetting of the roughened surface could be maintained while lowering the flow rate to down to 0.03 kg/cm-min. Unroughened (i.e smooth) sheets showed an initial minimum wetting rate of about 0.33 kg/cm-min.

It can be seen from the experiment that, were it not for the falling film element, the flow rate would be an order of magnitude greater. This would decrease the energy efficiency of the apparatus, since the pumping power is comparable in magnitude to the power supplied to thermoelectric elements. In addition, the gap inside each cell would be larger to contain the falling films, of thickness approximately proportional to the square root of the flow rate. Moreover, the single-phase heat flow through the falling film is reduced in a thicker falling film.

The invention claimed is:

1. An apparatus for purification of water comprising a plurality of thermoelectric modules in a horizontal arrangement, each of said modules comprising a hot side and a cold side, wherein at least a first hot surface is thermally coupled to said hot side and at least a first cold surface is thermally coupled to said cold side, said hot surface comprising means for contacting a liquid to said first hot surface, said means being selected from a falling film element or a porous, fibrous, fritted, sintered, patterned, finned, or carved wet evaporation element, wherein said first hot surface has an average surface roughness of between 1.2 and 50 micrometers and wherein a temperature of said hot surface is in a range of approximately 30 to 100° C. with the apparatus operating at an atmospheric pressure.

2. The apparatus according to claim 1, wherein said first hot surface has the average surface roughness of between 2 and 20 micrometers.

3. The apparatus according to claim 1, wherein a separation between said hot surface and said cold surface is between 1 and 40 mm.

4. The apparatus according to claim 1, wherein a separation between said hot surface and said cold surface is between 5 and 15 mm.

5. The apparatus according to claim 1, wherein a temperature of said cold surface is in a range of approximately 10 to 90° C., depending on a position of the thermoelectric module within the plurality of thermoelectric modules.

6. The apparatus according to claim 5, wherein the temperature of said hot surface is in the range of approximately 40 to 70° C. and the temperature of said cold surface is in the range of approximately 20 to 50° C.

7. The apparatus according to claim 1, wherein said apparatus further comprises a disinfecting element selected from the group consisting of a UV-lamp, a hypochlorite generator, a mixed oxidants generator, and an ozone generator.

8. The apparatus according to claim 1, wherein each of said thermoelectric modules comprises one evaporation half-cell and one condensation half-cell on opposing sides, each of said thermoelectric modules comprising sealing means.

9. The apparatus according to claim 1, wherein at least one of the hot surface or the cold surface is made from a metallic material or a thermoplastic polymer material.

10. The apparatus according to claim 9, wherein at least one of the hot surface or the cold surface is made from a metallic material selected from the group consisting of stainless steel, titanium, copper, aluminum and alloys thereof or from a thermoplastic polymeric material selected from the group consisting of polypropylene, polyethylene and mixtures thereof.

11. The apparatus according to 9, wherein said thermoplastic polymeric material further comprises copper-, graphite-, or nickel-based particles.

12. A method for purification of water, comprising the steps of:
  feeding a raw water feed to an apparatus for purification of water as set forth in claim 1,
  contacting at least a portion of said raw water feed to at least the hot surface,
  evaporating at the atmospheric pressure at least a part of said portion of said raw water feed to obtain a vapor stream,
  transporting said vapor stream to at least the cold surface, and
  condensing said vapor stream at said cold surface.

13. The method according to claim 12, wherein said first hot surface has an average surface roughness of between 2 and 20 micrometers.

14. The method according to claim 12, wherein the condensing step is carried out at a temperature in a range of approximately 10 to 90° C.

15. The method according to claim 12, wherein the condensing step is carried out at a temperature in a range of approximately 20 to 50° C.

16. The method according to claim 12, further comprising a step of remineralizing said condensed vapor stream.

17. A method according to claim 16, wherein the step of remineralizing said condensed vapor stream is carried out in a vessel external to said apparatus.

* * * * *